US009635449B2

(12) United States Patent
Lee

(10) Patent No.: US 9,635,449 B2
(45) Date of Patent: Apr. 25, 2017

(54) ACTIVE EARPHONE AUTHENTICATION METHOD

(71) Applicant: WISOL CO., LTD., Osan-si, Gyeonggi-do (KR)

(72) Inventor: Ahn Kook Lee, Suwon-si (KR)

(73) Assignee: WISOL CO., LTD., Osan-si, Gyeonggi-Do (KR)

( * ) Notice: Subject to any disclaimer, the term of this patent is extended or adjusted under 35 U.S.C. 154(b) by 0 days.

(21) Appl. No.: 14/734,475

(22) Filed: Jun. 9, 2015

(65) Prior Publication Data

US 2016/0192054 A1 Jun. 30, 2016

(30) Foreign Application Priority Data

Dec. 24, 2014 (KR) ........................ 10-2014-0188525

(51) Int. Cl.
*A61F 11/06* (2006.01)
*H04R 1/10* (2006.01)

(52) U.S. Cl.
CPC ....... *H04R 1/1041* (2013.01); *H04R 2460/01* (2013.01)

(58) Field of Classification Search
CPC .................................................... H04R 1/1041
See application file for complete search history.

(56) References Cited

U.S. PATENT DOCUMENTS

2011/0107415 A1* 5/2011 Shen ..................... G06F 21/445 726/19
2012/0148062 A1 6/2012 Scarlett et al.
2015/0043757 A1* 2/2015 Prentice ............ H04M 1/72527 381/150
2015/0296286 A1* 10/2015 Prentice ............... H04R 1/1083 381/71.6

FOREIGN PATENT DOCUMENTS

KR 10-2011-0097622 A 8/2011
KR 10-1473173 B1 12/2014

OTHER PUBLICATIONS

KIPO Office Action for Korean Patent Application No. 10-2014-0188525 which corresponds to the above-identified U.S. application.

* cited by examiner

*Primary Examiner* — Simon King
(74) *Attorney, Agent, or Firm* — LRK Patent Law Firm

(57) ABSTRACT

An active earphone authentication method includes a recognition step of recognizing insertion of an earphone by a terminal control unit; a voltage supply step of transmitting a voltage supply command to the power supply unit by the terminal control unit if insertion of the earphone is recognized at the recognition step; an authentication step of receiving a signal from the earphone and authenticating whether or not the earphone is an active earphone by a reception unit; and a circuit implementation step of implementing a circuit of the terminal equipment according to an authentication result of the authentication step.

7 Claims, 5 Drawing Sheets

200

ACTIVE EARPHONE AUTHENTICATION METHOD

BACKGROUND OF THE INVENTION

Field of the Invention

The present invention relates to an active earphone authentication method, and more specifically, to an active earphone authentication method for distinguishing an active earphone to which an Active Noise Cancelling (ANC) technique is applied by supplying voltage to the earphone by a terminal equipment from a general earphone to which the Active Noise Cancelling (ANC) technique is not applied.

Background of the Related Art

Since a user increases volume when background noises are severe, such an earphone device may act as a factor generating hearing impairment when the user listens to music or broadcast for an extended period of time. Active noise cancelling techniques (ANC) are introduced recently to improve quality of sound of the earphone device. The active noise cancelling technique (ANC) is a technique of analyzing frequencies, magnitudes, sound qualities and the like of various kinds of sounds flowing into the earphone device and offsetting noises by sending out sound waves of reverse wavelength through a speaker. Such an active noise cancelling technique (ANC) is stated in the 'Active Noise Cancelling System' disclosed in Korean Patent Publication No. 10-2011-0097622.

However, if the earphone device is changed to an earphone mode to which the Active Noise Cancelling (ANC) technique is not applied while power is supplied to the earphone device and a key button is pressed at the earphone device, excessive current flows through the earphone device.

SUMMARY OF THE INVENTION

An object of the present invention is to provide a terminal equipment which can support both a general earphone to which an Active Noise Cancelling (ANC) technique is not applied and an active earphone to which the Active Noise Cancelling (ANC) technique is applied.

In addition, another object of the present invention is to minimize the problem of flowing excessive current, even when voltage is supplied to the general earphone device.

To accomplish the above objects, according to one aspect of the present invention, there is provided an active earphone authentication method including the steps of: a recognition step of recognizing insertion of an earphone by a terminal control unit; a voltage supply step of transmitting a voltage supply command to the power supply unit by the terminal control unit if insertion of the earphone is recognized at the recognition step; an authentication step of receiving a signal from the earphone and authenticating whether or not the earphone is an active earphone by a reception unit; and a circuit implementation step of implementing a circuit of the terminal equipment according to an authentication result of the authentication step.

The authentication step may be a step of authenticating whether or not the earphone is an active earphone when the reception unit receives a frequency signal from the earphone.

The frequency signal may be a small signal having a predetermined frequency value.

The circuit implementation step may include a step of transmitting a voltage supply stop command to the power supply unit by the terminal control unit if it is determined at the authentication step that the inserted earphone is not an active earphone.

The voltage supply step may include a step of transmitting voltage to a microphone terminal of the earphone by the microphone reception terminal of the terminal equipment.

According to another aspect of the present invention, there is provided an active earphone authentication circuit including: a power supply unit for transmitting voltage to an earphone; a terminal control unit for determining insertion of the earphone and directing the Power supply unit to supply power if the earphone is inserted; a reception unit for sensing a frequency signal received from the earphone and determining whether or not the earphone is an active earphone; and a terminal host for implementing an active earphone circuit as a circuit of a terminal equipment if the earphone is determined as an active earphone by the reception unit.

The power supply unit may transmit voltage to a microphone terminal of the earphone.

The frequency signal may be a small signal having a predetermined frequency value.

If the inserted earphone is not an active earphone, the terminal control unit may transmit a voltage supply stop command to the power supply unit.

DETAILED DESCRIPTION OF THE PREFERRED EMBODIMENT

Details of the objects and technical configuration of the present invention described above and operational effects according thereto will be clearly understood hereinafter by the detailed description with reference to the accompanying drawings attached in the specification of the present invention.

The constitutional components expressed in this specification are merely examples for implementing the present invention. Accordingly, other components may be used in other implementations of the present invention without departing from the spirit and scope of the present invention. In addition, although each component can be implemented only in a pure hardware or software configuration, it also can be implemented by combining various hardware or software configurations performing the same function.

Expressions such as <voltage supply command>, <voltage supply circuit> and <supply voltage> of this specification may also be applied to all electrical signals which can be used in an earphone and may be applied and implemented like <electrical signal transmission command>, <electrical signal supply circuit> and <transmit an electrical signal>.

Figure 1:
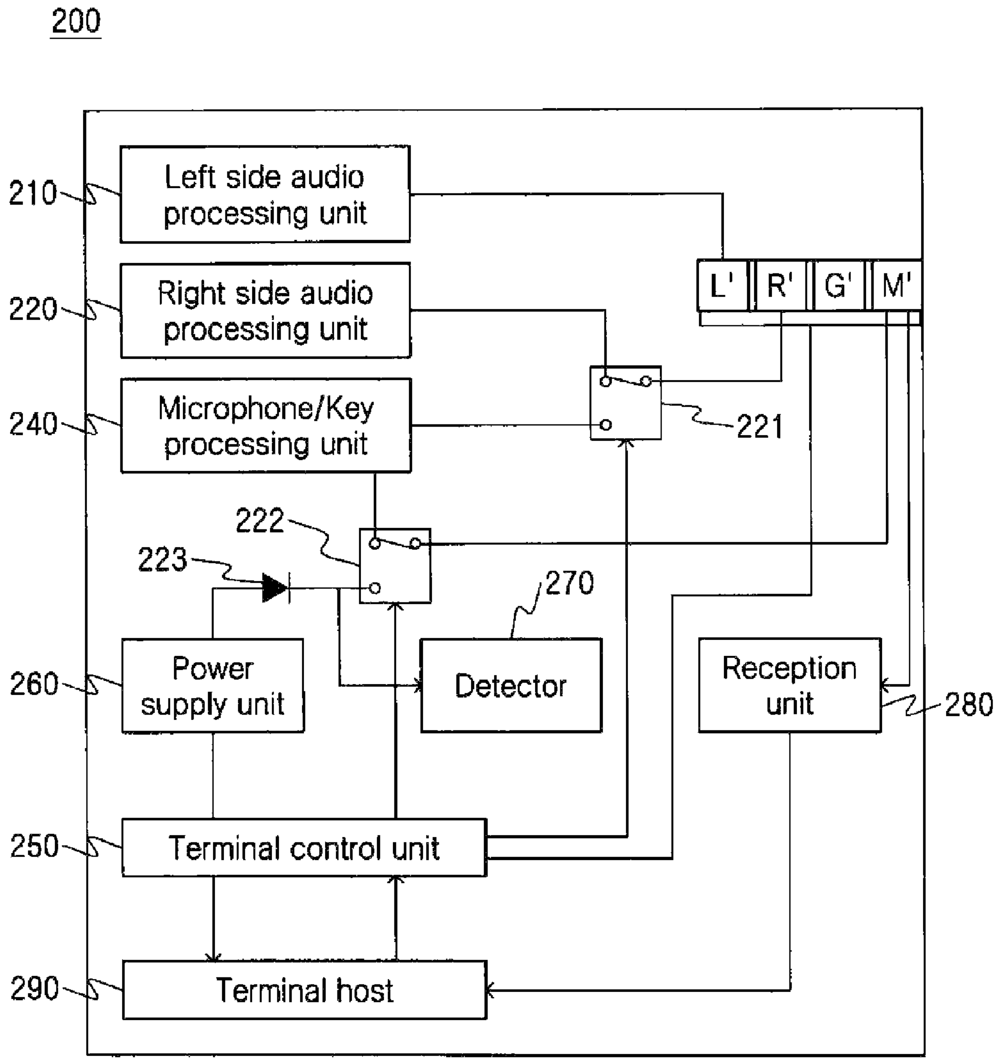
FIG. 1 is a circuit diagram schematically showing an active earphone authentication circuit according to an embodiment of the present invention.
Figure 2:
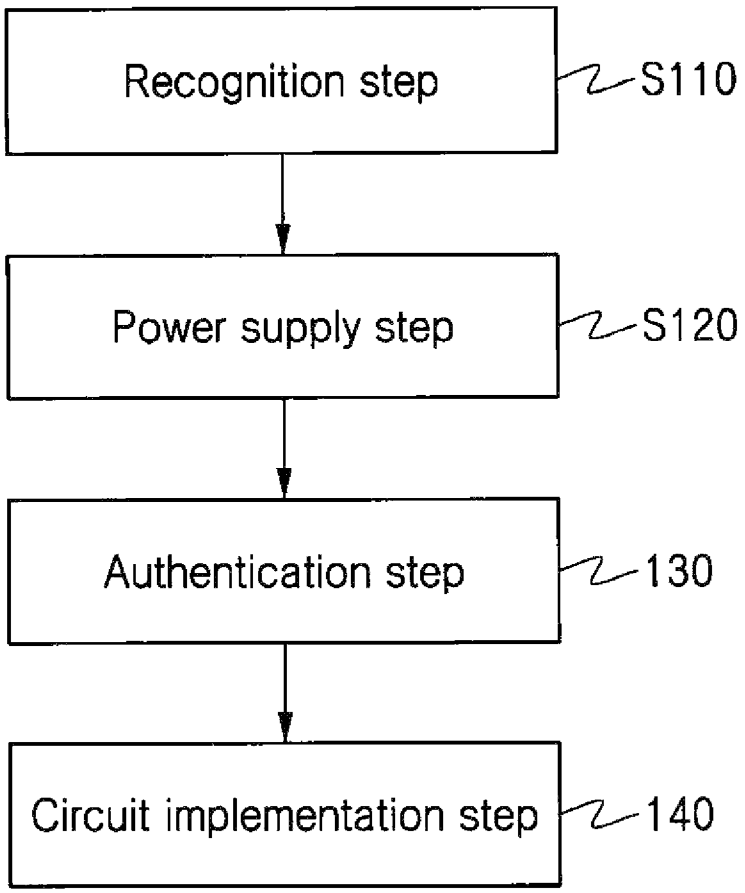
FIG. 2 is a flowchart schematically illustrating an active earphone authentication method according to an embodiment of the present invention.

FIG. 1 is a circuit diagram schematically showing an active earphone authentication circuit according to an embodiment of the present invention, and FIG. 2 is flowchart schematically illustrating an active earphone authentication method according to an embodiment of the present invention. Referring to FIGS. 1 and 2, an active earphone authentication method according to an embodiment of the present invention includes a recognition step S110 of recognizing insertion of an earphone by a terminal control unit 250 of a terminal equipment 200, a voltage supply step S120 of transmitting a voltage supply command to the power supply unit 260 by the terminal control unit 250 if insertion of the earphone is recognized at the recognition step S110, an authentication step S130 of receiving a signal from the earphone and authenticating whether or not the earphone is an active earphone by a reception unit 280, and a circuit implementation step S140 of implementing a circuit of the terminal equipment 200 according to an authentication result of the authentication step S130. The active earphone authentication method according to an embodiment of the present invention is a method of distinguishing whether an earphone is an active earphone or a general earphone by transmitting a voltage to an inserted earphone if insertion of the earphone is recognized and receiving a signal corresponding to the transmitted voltage.

Figure 3:
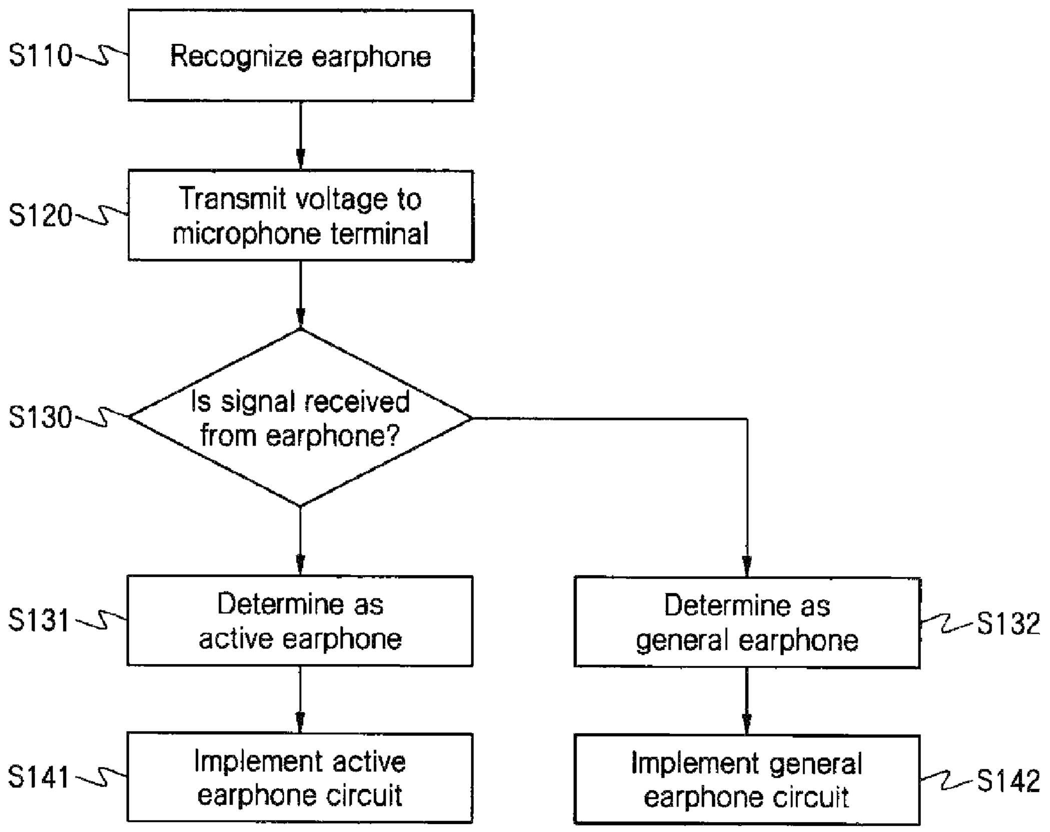
FIG. 3 is a flowchart schematically illustrating an active earphone authentication method according to an embodiment of the present invention.

FIG. 3 is a flowchart schematically illustrating an active earphone authentication method according to an embodiment of the present invention. Referring to FIG. 3, first, the earphone should be recognized by the terminal equipment 200. If the earphone is inserted into the terminal unit L', R', M' and G' of the terminal equipment 200, the terminal control unit 250 connected to the terminal unit L', R', M' and G' recognizes insertion of the earphone S110. If the terminal control unit 250 recognizes insertion of the earphone into the terminal unit L', R', M' and G', it transmits a voltage supply command to the power supply unit 260. At this point, the voltage supply command is a signal for supplying voltage from the power supply unit 260 to the earphone through the microphone reception terminal M'. In addition, at this point, the terminal control unit 250 cuts off the connection between the microphone reception terminal M' and a microphone/key processing unit 240 and connects the microphone reception terminal M' to the power supply unit 260 by turning off a second audio switch 222.

If the terminal equipment 200 transmits voltage to the earphone S120, a reception unit 280 connected to the microphone reception terminal M' senses a signal received from the microphone reception terminal M' S130. The authentication step S130 is a step of authenticating whether or not the earphone is an active earphone when the reception unit 280 receives a frequency signal from the earphone. If the reception unit 280 receives a signal from the microphone reception terminal M', the reception unit 280 determines the inserted earphone as an active earphone S131. At this point, the frequency signal is a small signal. At this point, the small signal is a small signal having a predetermined frequency. In addition, if the reception unit 280 does not receive a signal from the microphone reception terminal M' for a predetermined period of time, the reception unit 280 determines the inserted earphone as a general earphone S132.

If it is determined that the inserted earphone is an active earphone, the terminal equipment 200 should implement a circuit corresponding to the active earphone. The circuit implementation step S140 includes a step of transmitting a voltage supply stop command to the power supply unit 260 by the terminal control unit 250 if it is determined at the authentication step S130 that the inserted earphone is not an active earphone. If the inserted earphone is an active earphone, the terminal unit 200 continues supplying the voltage to the earphone. Basically, the microphone/key processing unit 240 of the terminal equipment 200 is connected to the microphone reception terminal M'. The second audio switch 222 is switched to connect the power supply unit 260 to the microphone reception terminal M' so that the terminal equipment 200 may supply voltage to the earphone at the voltage supply step S120. If the inserted earphone is an active earphone, the connection between the power supply unit 260 and the microphone reception terminal M' is maintained, and the terminal unit 200 continues supplying the voltage to the earphone.

If it is determined at the authentication step S130 that the inserted earphone is a general earphone S132, the terminal unit 200 implements a general earphone circuit S142. The general earphone circuit is a circuit in which the microphone/key processing unit 240 and the microphone reception terminal M' are connected. To this end, the connection between the microphone reception terminal M' and the power supply unit 260 is cut off and the microphone reception terminal M' is connected to the microphone/key processing unit 240 by turning on the second audio switch 222 which is turned off to supply voltage from the terminal equipment 200 to the earphone. In addition, connection between the right side audio processing unit 220 and the right side audio terminal R' is also maintained by maintaining the turned-on state of the first audio switch 221.

Figure 4:
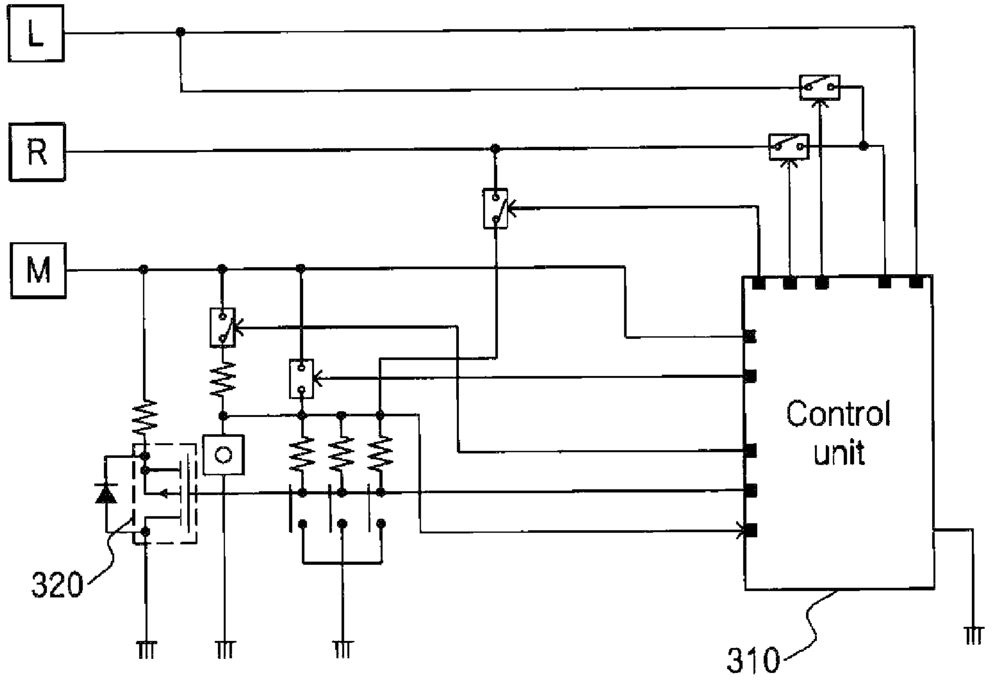
FIG. 4 is a circuit diagram schematically showing a circuit of an earphone according to an embodiment of the present invention.

FIG. 4 is a circuit diagram schematically showing a circuit of an earphone according to an embodiment of the present invention. If an earphone 300 is inserted into the terminal equipment 200 at the recognition step S110, the terminal equipment 200 supplies voltage to the earphone 300 at the voltage supply step S120. In the terminal equipment 200, the power supply unit 260 is connected to the microphone reception terminal M', and the power supply unit 260 supplies voltage to the microphone reception terminal M'. The earphone 300 inserted into the terminal equipment 200 is supplied with the voltage supplied to the microphone reception terminal M' through the microphone terminal M connected to the microphone reception terminal M'. The voltage supplied through the microphone terminal M is transmitted to the control unit 310 of the earphone 300.

If the earphone 300 supplied with the voltage through the microphone terminal M is an active earphone, the control unit 310 of the earphone 300 is supplied with the voltage and transmits a frequency signal to the terminal equipment 200 connected to the microphone terminal M through the microphone terminal M by transmitting the frequency signal to the FET 320. The reception unit 280 of the terminal equipment 200 receives the frequency signal transmitted from the earphone 300. If the reception unit 280 receives the frequency signal, the inserted earphone is determined as an active earphone. The reception unit 280 transmits information informing that the inserted earphone is an active earphone to a terminal host 290. If the earphone 300 supplied with the voltage through the microphone terminal M is a general earphone, the control unit of the earphone is not driven although the voltage is supplied and does not transmits any signal to the terminal equipment 200. If the reception unit 280 of the terminal equipment 200 does not receive a signal for a predetermined period of time, it determines the inserted earphone as a general earphone and transmits information informing that the inserted earphone is a general earphone to the terminal host 290.

If the terminal host 290 receives the information informing that the inserted earphone is an active earphone or a general earphone from the reception unit 280, it transmits a circuit implementation command signal to the terminal control unit 250 in order to implement a circuit corresponding to the active earphone or the general earphone. If the inserted earphone is an active earphone, the terminal host 290 transmits an active earphone circuit implementation command signal to the terminal control unit 250, and the terminal control unit 250 receiving the active earphone circuit implementation command signal implements an active earphone circuit by controlling a circuit. If the inserted earphone is a general earphone, the terminal host 290 transmits a general earphone circuit implementation command signal to the terminal control unit 250, and the terminal control unit 250 receiving the general earphone circuit implementation command signal implements a general earphone circuit by controlling a circuit.

Figure 5:
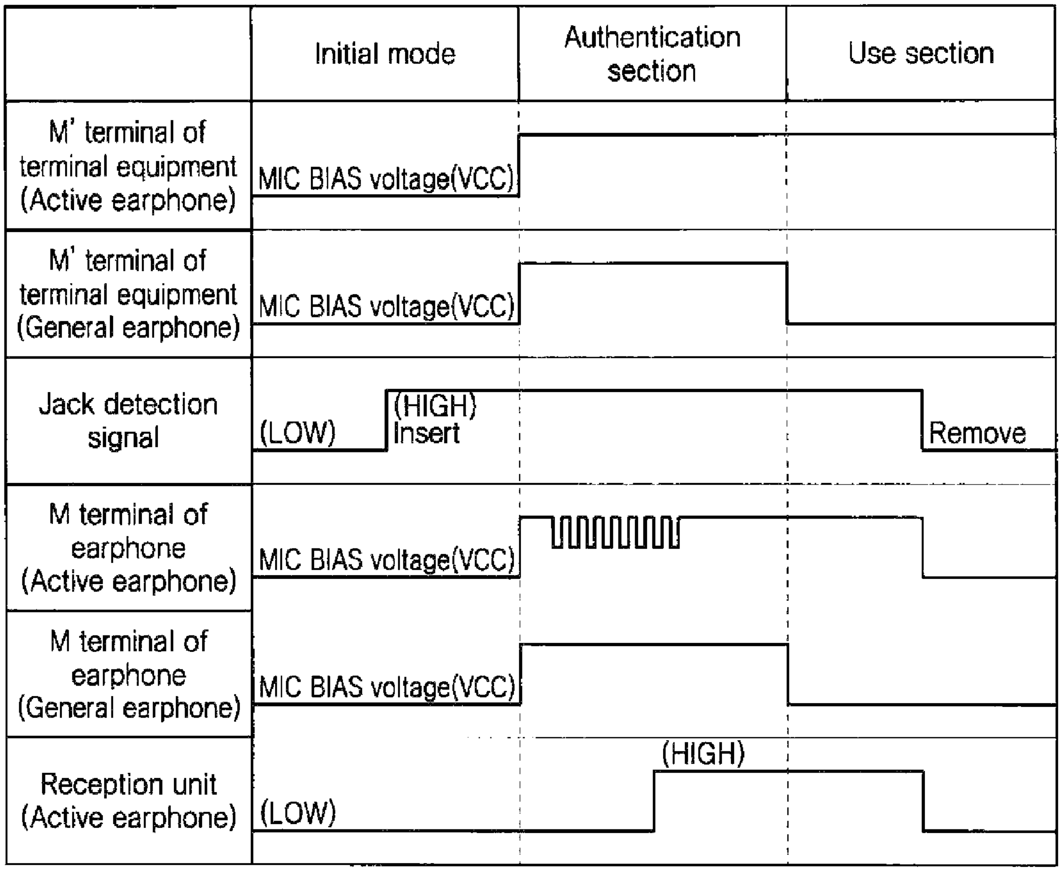
FIG. 5 is a table schematically showing signals of each step according to an embodiment of the present invention.

FIG. 5 is a table schematically showing signals of each step according to an embodiment of the present invention. Referring to FIG. 5, if the earphone 300 is an active earphone, the microphone reception terminal M' of the terminal equipment 200 transmits voltage in an authentication section, and if the earphone is authenticated as an active earphone, supply of the voltage is maintained in a use section. If the earphone is a general earphone, the microphone reception terminal M' of the terminal equipment 200 transmits voltage in the authentication section, and if the earphone is authenticated as a general earphone, supply of the voltage is stopped in the use section.

A Jack detection signal is a signal for recognizing insertion of an earphone by the terminal control unit 250 when the earphone is inserted. The Jack detection signal maintains voltage from the insertion to the removal of the earphone during the sections starting from the initial mode to the use section. The Jack detection signal is divided into low voltage when the earphone is inserted and high voltage when the earphone is removed. At this point, the voltage is a signal for receiving the earphone insertion information from the terminal control unit 250.

If the earphone 300 is an active earphone, the microphone terminal M of the earphone senses a frequency signal in the authentication section. At this point, the frequency signal is a signal for authenticating the earphone 300 as an active earphone by transmitting the frequency signal to the microphone terminal M by the control unit 310 of the earphone 300 when voltage is supplied to the earphone 300. If the earphone 300 is an active earphone, since the microphone terminal M is supplied with voltage from the terminal equipment 200 in the use section, the voltage is maintained, and then if the earphone 300 is removed from the terminal equipment 200, the voltage is changed to MIC BIAS voltage and thus changed to the voltage of the initial mode.

If the earphone is a general earphone, although the microphone terminal M of the earphone senses a voltage received from the terminal equipment 200 to authenticate whether the earphone is a general earphone or an active earphone in the authentication section, supply of the voltage is stopped in the use section after the earphone is authenticated as a general earphone. If the earphone 300 is an active earphone, the reception unit 280 of the terminal equipment 200 receives the frequency signal transmitted from the microphone terminal M of the earphone 300 and thus receives voltage at a point in the authentication section. At this point, the voltage is the frequency signal transmitted from the control unit 310 of the earphone 300 and received by the reception unit 280 of the terminal equipment 200, which is restored to a frequency signal of a small signal. If the earphone 300 is removed from the terminal equipment 200, the voltage received by the reception unit 280 of the terminal equipment 200 is also changed and initialized to the MIC BIAS voltage.

An active earphone authentication circuit according to an embodiment of the present invention includes a power supply unit 260 for transmitting voltage to an earphone, a terminal control unit 250 for determining insertion of the earphone and directing the power supply unit 260 to supply power if the earphone is inserted, a reception unit 280 for sensing a frequency signal received from the earphone 300 and determining whether or not the earphone is an active earphone, and a terminal host 290 for implementing an active earphone circuit as a circuit of a terminal equipment if the earphone is determined as an active earphone by the reception unit 280. The power supply unit 260 transmits voltage to the microphone terminal of the earphone. At this point, the frequency signal is a small signal having a predetermined frequency value. If the inserted earphone is not an active earphone, the terminal control unit 250 transmits a voltage supply stop command to the power supply unit 260.

Since the detailed description of the active earphone authentication circuit according to an embodiment of the present invention is different from the active earphone authentication method described above with reference to FIGS. 1 to 5 only in category and includes the same information, it will be omitted.

The present invention has an effect of providing a terminal equipment capable of supporting both a general earphone device and an earphone device to which an active noise cancelling technique is applied.

In addition, the present invention has an effect of minimizing the problem of flowing excessive current, even when voltage is supplied to a general earphone device.

The embodiments disclosed in the present invention are provided not to limit the technical concept of the present invention but to illustrate the technical concept of the present invention. Therefore, the scope of the technical concept of the present invention is not limited by such embodiments. The scope of the protection of the present invention should be determined by reasonable interpretation of the appended claims and all technical concepts coming within the equivalency range of the present invention should be interpreted to be embraced in the scope of the right of the present invention.

What is claimed is:

1. An active earphone authentication method comprising:

a recognition step of recognizing insertion of an earphone by a terminal control unit;

a voltage supply step of transmitting a voltage supply command to a power supply unit by the terminal control unit if the insertion of the earphone is recognized at the recognition step;

an authentication step of receiving a signal from the earphone and authenticating whether or not the earphone is an active earphone by a reception unit; and a circuit implementation step of implementing a circuit of terminal equipment according to an authentication result of the authentication step, wherein when the earphone is authenticated as an active earphone, the voltage supply is maintained, and wherein the circuit implementation step includes a step of transmitting a voltage supply stop command to the power supply unit by the terminal control unit if it is determined at the authentication step that the earphone is not an active earphone.

2. The method according to claim 1, wherein the authentication step is a step of authenticating whether or not the earphone is an active earphone when the reception unit receives a frequency signal from the earphone.

3. The method according to claim 2, wherein the frequency signal is a signal having a predetermined frequency value.

4. The method according to claim 1, wherein the voltage supply step includes a step of transmitting a voltage to a microphone terminal of the earphone by a microphone reception terminal of the terminal equipment.

5. An active earphone authentication, circuit comprising:

a power supply unit for transmitting a voltage to an earphone;

a terminal control unit for determining insertion of the earphone and directing the power supply unit to supply power if the earphone is inserted;

a reception unit for sensing a frequency signal received from the earphone and determining whether or not the earphone is an active earphone; and a terminal host for implementing an active earphone circuit as a circuit of terminal equipment if the earphone is determined as an active earphone by the reception unit, wherein when the earphone is authenticated as an active earphone, the voltage supply is maintained, and wherein if the inserted earphone is not an active earphone, the terminal control unit transmits a voltage supply stop command to the power supply unit.

6. The circuit according to claim 5, wherein the power supply unit transmits a voltage to a microphone terminal of the earphone.

7. The circuit according to claim 5, wherein the frequency signal is a signal having a predetermined frequency value.

* * * * *